(12) United States Patent
Ruys et al.

(10) Patent No.: US 11,378,535 B2
(45) Date of Patent: Jul. 5, 2022

(54) MEASURING PROBE FOR MEASURING IN GROUND A PARAMETER AND A METHOD FOR MAKING SUCH A PROBE

(71) Applicant: Sensoterra B.V., Amsterdam (NL)

(72) Inventors: Jurriaan Ruys, Amsterdam (NL); Eduard Zanen, Oudeschild (NL); Daan Roethof, Amsterdam (NL); Roche Boedhoe, The Hague (NL)

(73) Assignee: Sensoterra B.V., Amsterdam (NL)

( * ) Notice: Subject to any disclaimer, the term of this patent is extended or adjusted under 35 U.S.C. 154(b) by 108 days.

(21) Appl. No.: 16/472,599

(22) PCT Filed: Dec. 22, 2017

(86) PCT No.: PCT/EP2017/084412
§ 371 (c)(1),
(2) Date: Jun. 21, 2019

(87) PCT Pub. No.: WO2018/115454
PCT Pub. Date: Jun. 28, 2018

(65) Prior Publication Data
US 2020/0150067 A1    May 14, 2020

(30) Foreign Application Priority Data
Dec. 23, 2016   (NL) .................................... 1042193

(51) Int. Cl.
*G01N 27/07* (2006.01)
*G01N 27/04* (2006.01)
*G01N 33/24* (2006.01)

(52) U.S. Cl.
CPC ........... *G01N 27/07* (2013.01); *G01N 27/048* (2013.01); *G01N 33/246* (2013.01)

(58) Field of Classification Search
CPC ........ G01N 27/00; G01N 27/02; G01N 27/04; G01N 27/048; G01N 27/06; G01N 27/07;
(Continued)

(56) References Cited

U.S. PATENT DOCUMENTS

| | | | | |
|---|---|---|---|---|
| 3,582,768 A | * | 6/1971 | Watson | G01N 33/1886 324/449 |
| 3,968,428 A | * | 7/1976 | Numoto | G01N 27/041 324/694 |

(Continued)

FOREIGN PATENT DOCUMENTS

| | | |
|---|---|---|
| DE | 37 02 725 A1 | 8/1988 |
| DE | 299 08 134 U1 | 7/1999 |

OTHER PUBLICATIONS

PCT/EP2017/084412, Mar. 23, 2018, International Search Report and Written Opinion.
(Continued)

*Primary Examiner* — Hoai-An D. Nguyen
(74) *Attorney, Agent, or Firm* — Wolf, Greenfield & Sacks, P.C.

(57) ABSTRACT

A measuring probe for measuring in ground a parameter, the probe having an elongate body with a tip as a leading end and a head as a trailing end, the elongate body having a first and a second member which each extend in a longitudinal direction of the elongate body, the second member provides resistance against bending of the first member when the tip is advanced into the ground by hammering on the head.

19 Claims, 8 Drawing Sheets

(58) Field of Classification Search
CPC .... G01N 27/22; G01N 27/223; G01N 27/226; G01N 33/00; G01N 33/24; G01N 33/246
USPC .... 324/600, 649, 691; 702/47, 53, 127, 130, 702/133
See application file for complete search history.

(56) References Cited

U.S. PATENT DOCUMENTS

| | | | | |
|---|---|---|---|---|
| 4,219,776 | A * | 8/1980 | Arulanandan | G01R 27/26 324/323 |
| 4,264,902 | A * | 4/1981 | Miller | G08B 21/20 340/602 |
| 4,616,425 | A * | 10/1986 | Burns | G01N 27/223 324/667 |
| 4,860,753 | A * | 8/1989 | Amerena | A61B 5/0531 600/306 |
| 4,929,885 | A | 5/1990 | Dishman | |
| 5,730,024 | A * | 3/1998 | Sahlen | G01N 33/383 73/73 |
| 5,908,267 | A * | 6/1999 | Schuring | B09C 1/067 405/128.65 |
| 11,215,602 | B2 * | 1/2022 | Pluta | G01V 3/15 |
| 11,231,350 | B2 * | 1/2022 | Karabacak | G01N 3/068 |
| 2002/0165700 | A1 * | 11/2002 | Zur | A01G 25/165 702/188 |
| 2016/0223511 | A1 * | 8/2016 | Koshnick | G01N 33/24 |
| 2017/0082568 | A1 | 3/2017 | Pillai et al. | |
| 2020/0080270 | A1 * | 3/2020 | Landskroon | G01V 1/44 |
| 2021/0195857 | A1 * | 7/2021 | Haran | G08C 17/00 |
| 2021/0302349 | A1 * | 9/2021 | Jung | G01N 27/228 |

OTHER PUBLICATIONS

International Search Report and Written Opinion for International Application No. PCT/EP2017/084412, dated Mar. 23, 2018.

* cited by examiner

MEASURING PROBE FOR MEASURING IN GROUND A PARAMETER AND A METHOD FOR MAKING SUCH A PROBE

CROSS-REFERENCE TO RELATED APPLICATIONS

This application is a national stage filing under 35 U.S.C. § 371 of international application number PCT/EP2017/084412, filed Dec. 22, 2017, which claims the benefit of Dutch application number 1042193, filed Dec. 23, 2016, each of which is herein incorporated by reference in its entirety.

The disclosure relates to a measuring probe for measuring in ground a parameter, and to a method for producing such a measuring probe.

BACKGROUND

In the field of agriculture, or even more general in the field of management of a large piece of ground for the purpose of growth of at least certain plant species, it is often considered advantageous and helpful to know certain parameters of the soil.

Let's take as an example irrigation of land which is often needed and carried out in areas where water is not widely available. Ideally, water is only supplied to land when there is a need for the supply of the water. When water is supplied, ideally not more than necessary is supplied. The optimization can be assisted by, or based on, the availability of data which reveal the present amount of moisture in the ground at a meaningful level from the surface. To that end, measuring probes are brought into the ground. Although reference is here made to measuring moisture, in principle measuring probes can, alternatively, or additionally, be dedicated to measuring other parameters, such as salinity, temperature etc.

In the following, the terms ground and soil are interchangeably used. However, these terms are meant to embrace more than ground that is established as fit for agriculture. For instance also very dry ground, or even sandy ground with large particles (stones) in a somewhat rocky area is meant to be covered by the term ground as used in this disclosure.

A measuring probe can be installed in the ground in a number of different ways. One could dig a hole, place the probe in the hole, and fill the hole up again. This is time consuming and disturbs the soil. One could possibly drill a hole. Such a method is for example disclosed in U.S. Pat. No. 4,929,885, in which first a hole is drilled with an auger. This requires special equipment that needs to be operated by relatively skilled users and that needs to be well maintained. One could add water to the soil, if that is considered helpful. This requires the local supply of water at the very spot where the probe will be installed, is time consuming, and requires much coordination. One could also drive a probe into the ground in a way a screw is driven by a screwdriver into wood. This also requires special equipment, a specially designed probe, and often pre-drilling a hole. It may well be that these ways of installing a probe allow for measuring soil parameters at a relatively deep level.

US 2004/0207382 A1 describes a soil penetrating electrode that is made from metal that is hard enough to be hammered into the earth or soil, yet ductile enough to prevent shattering when hit. Whilst this requires in terms of labour skills and equipment very little, the probe cannot be hammered very deeply into the ground. The probe disclosed in US 2004/0207382 has a total length of 6 inches, i.e. slightly more than 15 cm. It is often desired to have information on soil parameters at deeper, even much deeper, levels in the ground.

It is desirable to have a probe that offers a solution to the conflicting requirements of straightforwardly installable and deeply installable.

SUMMARY OF THE DISCLOSURE

Provided is a measuring probe for measuring in ground a parameter. The probe has an elongate body with a tip as a leading end and a head as a trailing end. The elongate body has a first and a second member which each extend in a longitudinal direction of the elongate body. The first member may have, relative to the second member, a high impact strength. The second member may provide resistance against bending of the first member when the tip is advanced into the ground by hammering on the head. For that purpose, the second member itself is stiff in a sense that it strongly resists bending, particularly relative to the first member. It is even possible that the second member has also a high impact strength (even relative to the first member) when hit, for instance by a hammer, causing an "impact" in a longitudinal direction of the second member. It is for such an embodiment possible that the first member has overall relatively poor mechanical properties. The first member may be considered to be a body comprising components that are connected for functioning of the probe after installation in the ground. Advantageously, a probe as proposed by the present disclosure tends to remain straight when the tip of the probe is put on the ground, the elongate body is aligned with the direction of gravity, and the head is hammered on for forcing the probe into the ground. This facilitates installing into the ground a lengthy and thin probe, with simple and widely available means such as a hammer and by any laborer who is fit enough to use that hammer over a wide range of motion. As the probe advances into the ground, the ground itself will provide resistance against bending of the part that is already in the ground. The part that is still sticking upwardly out of the ground becomes more and more resistant against bending due to it becoming shorter and shorter with each stroke of the hammer reducing the distance between the head and the surface of the ground. The probe, once installed in this straightforward manner, allows for obtaining data at a larger depth from the surface.

DETAILED DESCRIPTION OF THE INVENTION

In the drawing, like parts have like references.

Figure 1:
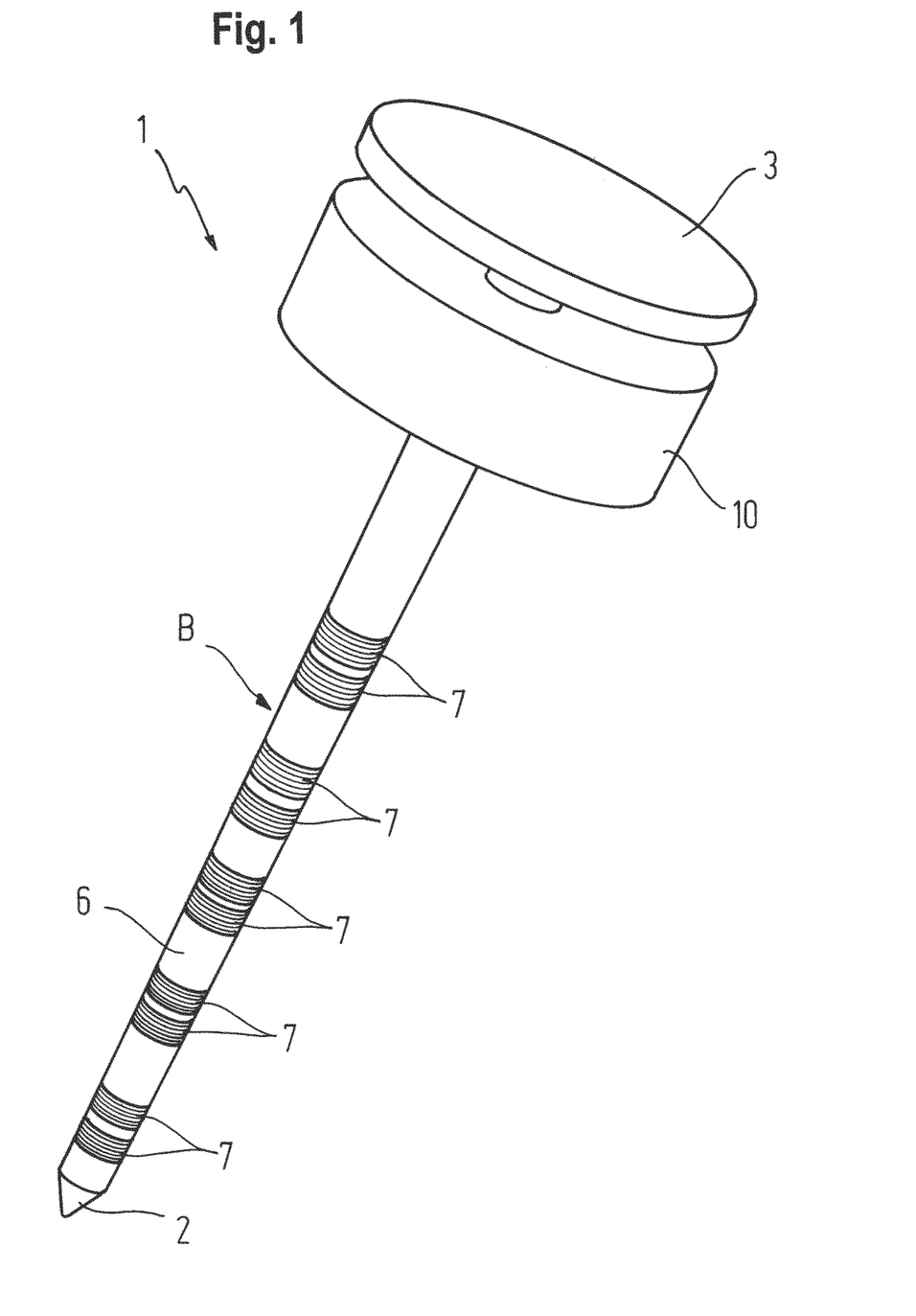
FIG. 1 shows a perspective view of an example of a measuring probe according to the present disclosure.

FIG. 1 shows in a perspective view a measuring probe 1 for measuring in ground a parameter. The probe 1 has an elongate body B with a tip 2 at the leading end and a head 3 at the trailing end. The term "leading end" refers to the use wherein the tip will be placed onto the ground and "leading the way" into the ground. As the tip 2 advances into the ground, the head 3 is basically trailing behind, i.e., following the probe as a part of the elongate body B that advances into the ground.

Figure 2:
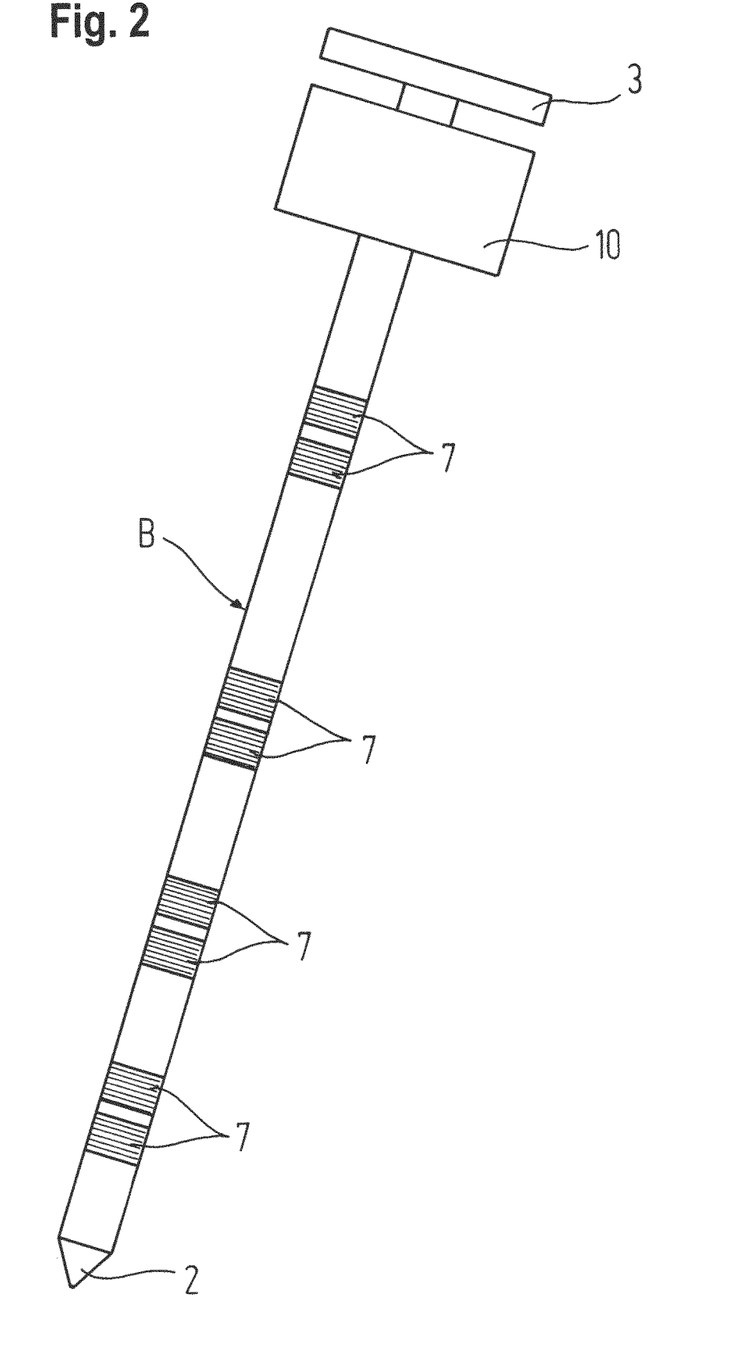
FIG. 2 shows a side view of the example of a measuring probe according to the disclosure.

For the avoidance of misinterpreting the perspective view presented in FIG. 1, a side view of the measuring probe 1 is provided in FIG. 2.

Figure 3:
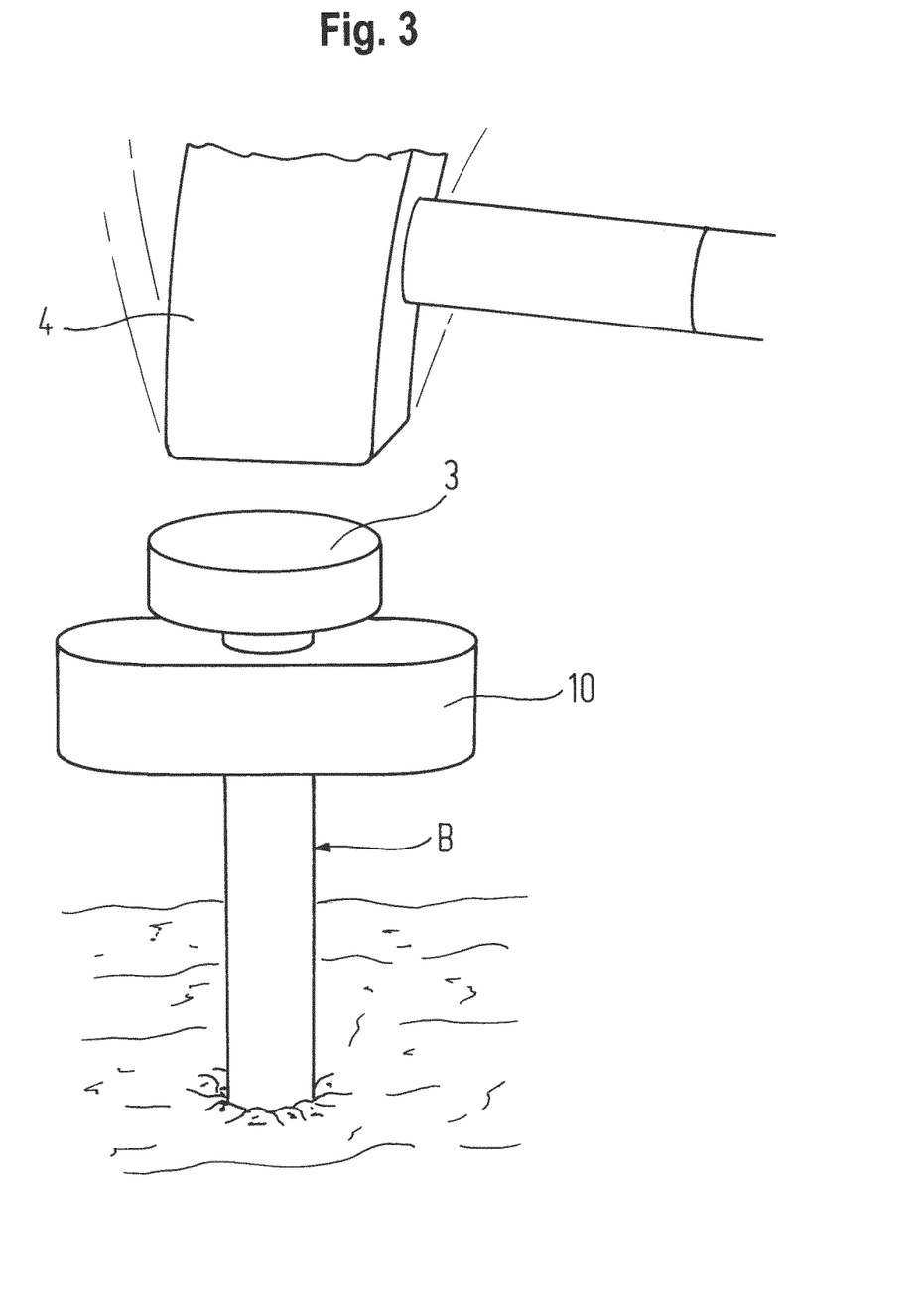
FIG. 3 shows views of an example of a measuring probe according to the disclosure.

FIG. 3 shows how in practice the measuring probe 1 may be brought into the ground. Basically, the tip is advanced into the ground by hammering on the head 3, for instance using a hammer 4.

Figure 4:
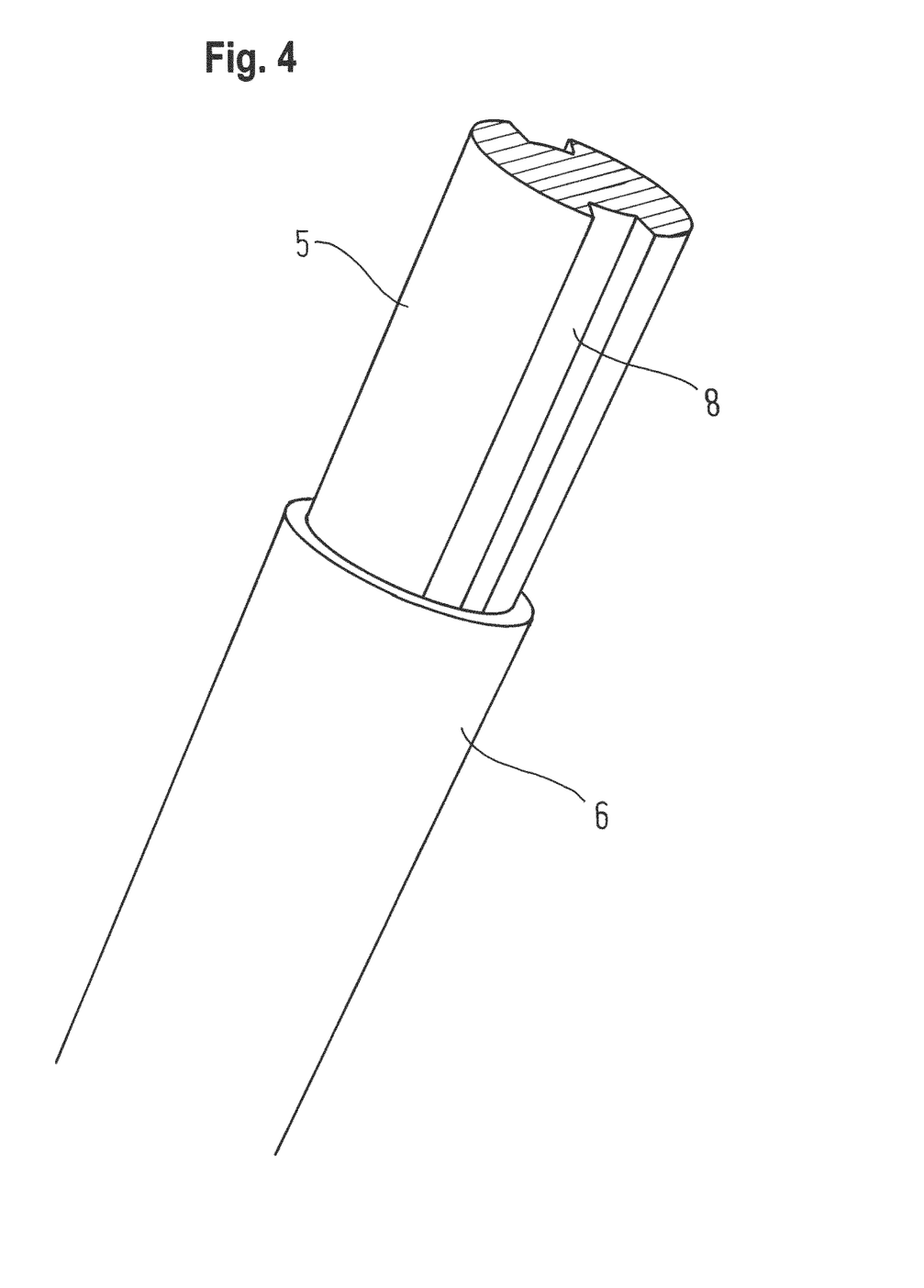
FIG. 4 shows a perspective view of a first member and a second member of an example of a measuring probe according to the disclosure.
Figure 5:
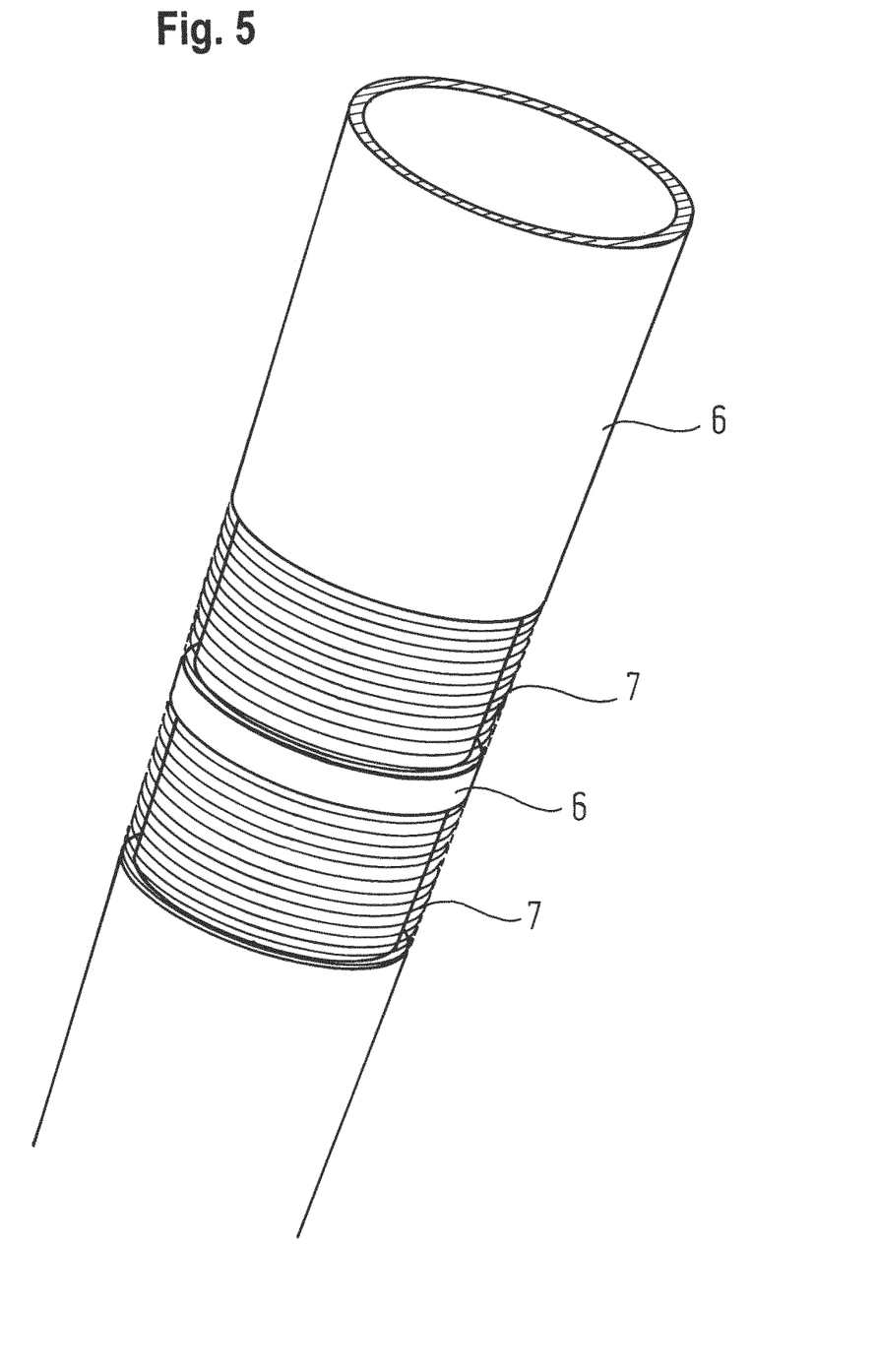
FIG. 5 shows in more detail a part of an example of a measuring probe according to the disclosure.
Figure 6:
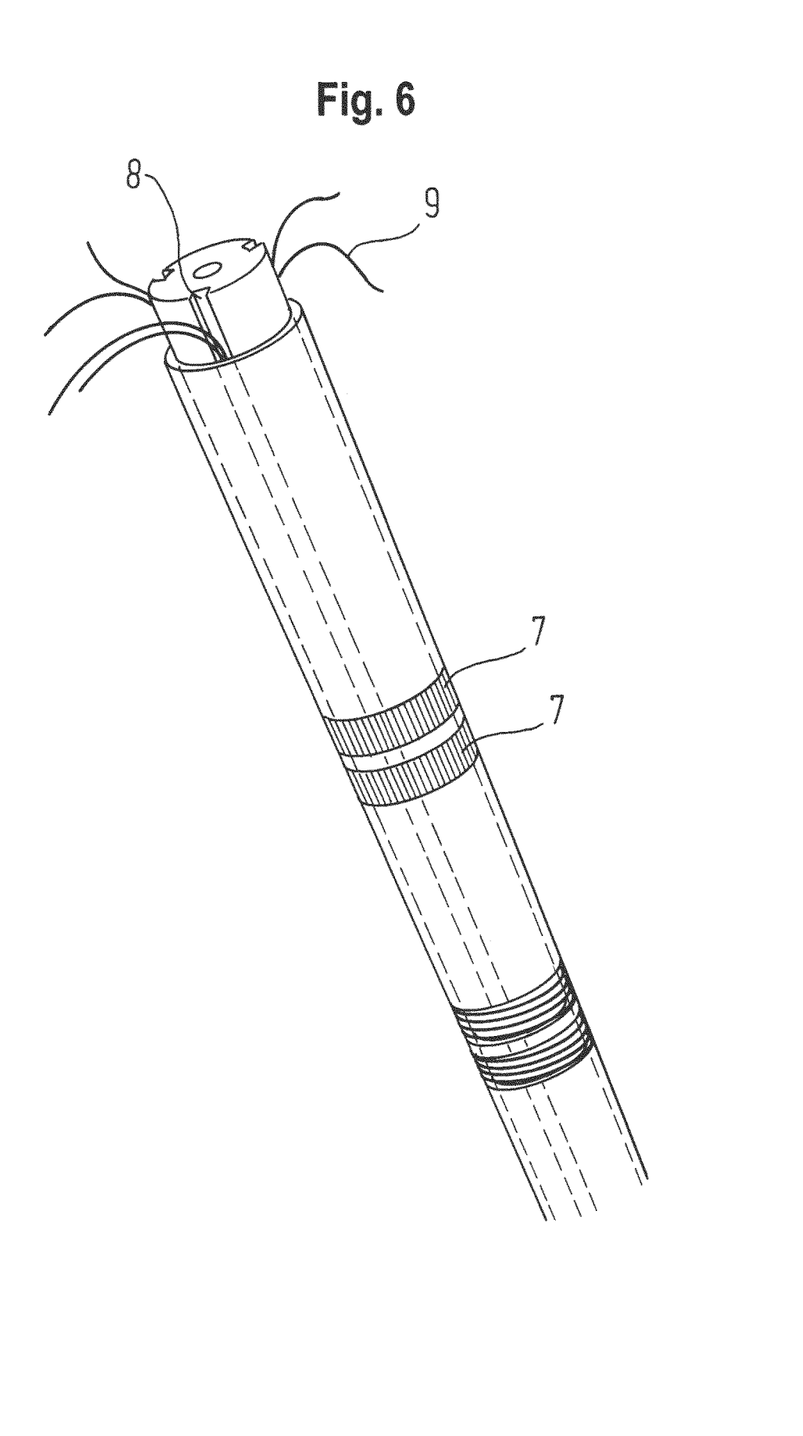
FIG. 6 shows in more detail a part of an example of a measuring probe according to the disclosure.

FIG. 4 shows parts of the elongate body B which, generally speaking, has according to an embodiment of the present disclosure, a first member 5 and a second member 6 which each extend in a longitudinal direction of the elongate body. The first member 5 and the second member 6 are in FIG. 4 shown as put together in a way that explains their relative position in lateral direction. That is, FIG. 4 not necessarily shows their exact relative axial position. The second member 6 provides resistance against bending, particularly relative to the first member. The second member provides resistance against bending of the first member 5 when the tip 2 is advanced into the ground by hammering on the head 3. Further features of the probe 1 are describes below.

Preferably, the first member 5 has relative to the second member a high impact strength. However, it is also conceivable that the second member has a high impact strength relative to the first member. The mechanical properties of the first member are then not that relevant. The second member 6 is in this example basically around the first member 5. Although it is shown that second member 6 is fully around first member 5, it is not inconceivable that second member 6 is provided with a slit extending in a longitudinal direction so that strictly speaking second member 6 is not fully around first member 5. Although, as shown, second member 6 preferably embraces first member 5, it is not inconceivable that the second member 6 is embraced by the first member 5, and that the second member 6 in that configuration still provides resistance against bending of the first member 5 when the tip is advanced into the ground by hammering on the head 3. The second member then acts more like a "backbone" of the elongate body B.

The measuring probe 1 further discussed in this description, has a second member 6 around the first member 5. The second member 6 is preferably pipe-shaped and the first member 5 is preferably bar-shaped.

It is possible that the second member 6 extends over a length which is shorter than the length over which the first member 5 extends. The tip 2 extends in longitudinal direction beyond the second member 6, as derivable from FIGS. 1 and 2.

Figure 8:
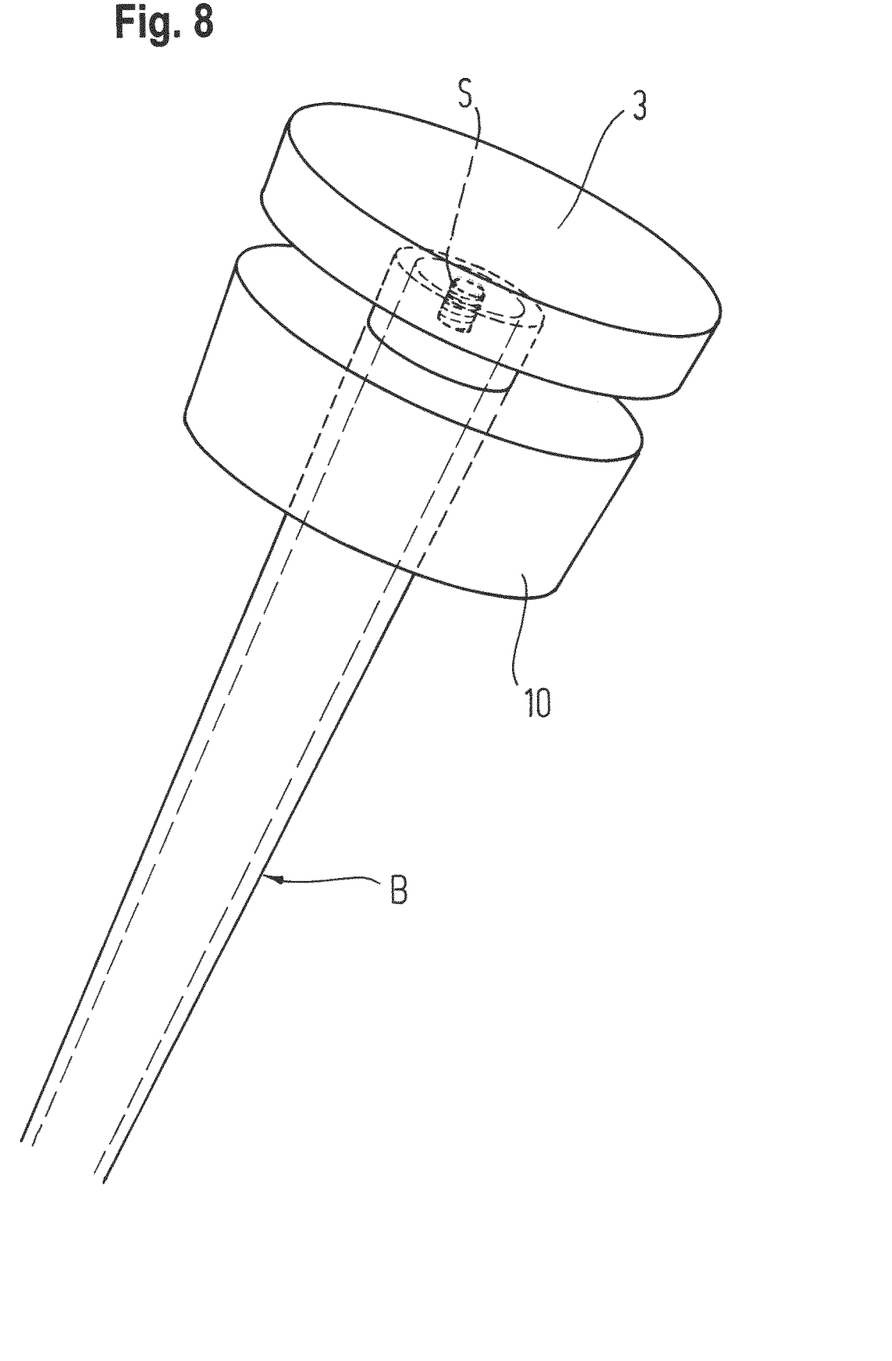
FIG. 8 shows schematically and in more detail a part of an example of a measuring probe according to the disclosure.

Preferably, the head 3 extends in longitudinal direction beyond the second member 6, as shown in FIG. 8. With further reference to FIG. 8, the head is preferably of metal. Preferably, the head is connected to the first member 5, ideally such that the axis of the first member 5 and the axis of the head 3 coincide. The elongate body B can for instance be provided with a screw S, which form a connection between the first member 5 and the head 3. Also other ways of connecting the head 3 and the first member 5 are conceivable.

Figure 7:
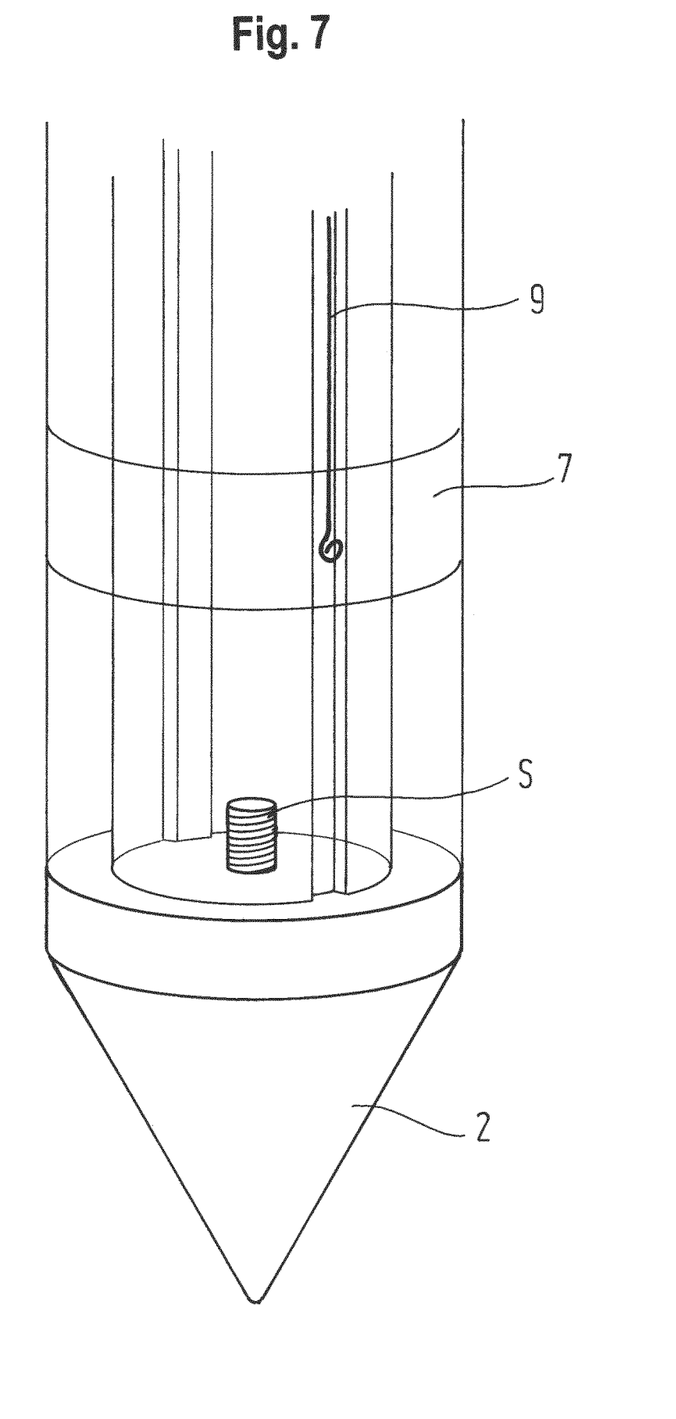
FIG. 7 shows in more detail a part of an example of a measuring probe according to the disclosure.

With reference to FIG. 7, the tip is preferably of metal. Further, the tip 2 is preferably connected to the first member 5, and ideally such that the axis of the first member 5 and the axis of the tip 2 coincide. Also here it may apply that the elongate body B is provided with a screw S, which forms a connection between the first member 5 and the tip 2. The tip 2 is, as shown, preferably conical, or otherwise shaped so as to facilitate advancing into the ground. The elongate body is preferably cylindrical. The diameter at the base of the cone preferably corresponds to the diameter of the elongate body B.

The first member 5 comprises or is preferably of an engineered stiff polymer material, such as polyoxymethelene (POM). Such an engineered stiff polymer material, as used for the first member 5, preferably allows for machining a groove and/or a thread. This facilitates manufacturing the probe and, respectively, installing electrical connections in a suitable way.

The second member 6 preferably comprises a fiber-reinforced material and/or carbon-based material.

The elongate body B is further preferably provided with a number of electrodes 7. The electrodes 7 are separated in the longitudinal direction of the elongate body. Ideally sets of electrodes 7 are positioned at different axial positions of the elongate body B. The electrodes 7 may be provided on the outside of the elongate body B. The electrodes are then preferably flush with the outer surface of the elongate body B, so that the electrodes do not provide resistance when the measuring probe is advanced into the ground.

Alternatively, the electrodes may be incorporated within the elongate body B and unexposed on the outer side of the elongate body. This still allows for measuring capacity of the ground for instance. For such measurements it is not needed that the electrodes 7 are in direct contact with the ground. The electrodes 7 may then be arranged on an outer surface of the first member 5. Also then, the electrodes are preferably flush with the outer side of the first member 5.

Preferably, the measuring probe 1 is provided with an IC board of which a central position and its connection point with the first member 5 coincide with the axis of the first member 5.

Preferably, the measuring probe 1 comprises between the second member 6 and the first member 5 parts 8 for electrical connections 9 extending between the respective electrodes 7 and the IC board (not shown).

Using the electrodes 7, the measuring probe can measure in the ground a parameter. Such a parameter may relate to at least one of: moisture content in the soil, pH, temperature, salinity, capacity, electrical conductivity. Although electrodes facilitate such measuring, it is not inconceivable that the probe can be equipped with other sensors (other than electrodes) for measuring other parameters in the ground.

The elongate body B is preferably cylindrical. The elongate body preferably has preferably a length which is larger than 45 cm, preferably larger than 55 cm and even more preferably larger than 65 cm. The elongate body has preferably a maximum thickness of 2.54 cm, even more a maximum thickness of 2 cm and even more preferably a maximum thickness of 1.8 cm. Clearly, it is preferred to have a long and thin elongate body B, so as to have little resistance when the probe is advanced into the ground, and to allow for reaching relatively deep levels in the ground.

The probe 1 is preferably provided with a casing 10 for encapsulating the IC board (not shown). The casing 10 may also house an antenna (not shown) for wireless transmission of data and/or determining GPS data of the probe 1. The casing 10 may also house a battery (not shown), ideally having a long operational lifetime.

The head 3 preferably "covers" the casing 10, so that the casing 10 is somewhat protected by the head 3 against accidentally being hit by a hammer when the probe 1 is being hammered into the ground.

Although not shown, the head 3 is preferably provided with a structure for connecting with a leverage-assembly for pulling the probe 1 out of the ground. Such a structure may be a hole, a hook, a lip, or anything else that allows for "grapping" the head, so as to push it upwardly out of the ground, or so as to pull it upwardly out of the ground.

Although it is very feasible to provide a bar-shaped first member 5, for instance by machining a polyoxymethelene (POM) material, the present disclosure and also envisages another method for producing a measuring probe 1 that can be advanced into the ground by hammering it and that is suitable for then measuring in the ground a parameter. Such a method comprises: providing a pipe-shaped member; arranging in the pipe-shaped member electrodes 7 and/or electrical connections 9; bringing into the pipe-shaped member a material having a composition, wherein the material is in a flowable condition during the bringing-in; and having the material harden after the bringing-in. Preferably the pipe-shaped member 6 comprises a fiber-reinforced material 10 or a carbon-based material. Preferably, the material having a composition comprises a thermoharder, such as an epoxy.

This method provides for the production of a very solid elongate body B, in which the electrical connections are incorporated in a fashion that not loosening can occur when the probe is being hammered into the ground.

A measuring probe according to the present disclosure may be a part of a system that allows for locally measuring parameters at a number of different position (in depth) and a number of different lateral position on (or rather in) a piece of land; transmitting these to a central position, and presenting these in a format that allows for taking suitable management decisions as to how to use and/or change the parameters as measured. A full description of such a system is, however, beyond the scope of the present disclosure.

The invention claimed is:

1. A measuring probe for measuring a soil parameter at a level deeper than 15 cm in the ground, the probe having an elongate body with a tip as a leading end and a head configured to be hammered on, for forcing the probe into the ground, as a trailing end, the elongate body comprising:
    a plurality of electrodes configured to measure the soil parameter at a level deeper than 15 cm in the ground after installation into the ground, the plurality of electrodes being located between the tip and the head and separated in a longitudinal direction of the elongate body, the plurality of electrodes including multiple sets of electrodes positioned at different axial positions in the longitudinal direction of the elongate body, and
    a first member and a second member which each extend in a longitudinal direction of the elongate body, the first member being connected to the head and the second member providing resistance against bending when the tip is advanced into the ground by hammering on the head.

2. The measuring probe according to claim 1, wherein the second member provides resistance against bending of the first member when the tip is advanced into the ground by hammering on the head.

3. The measuring probe according to claim 1, wherein the second member is around the first member.

4. The measuring probe according to claim 1, wherein the second member is pipe-shaped and the first member is bar-shaped.

5. The measuring probe of claim 1, provided with a casing for encapsulating an IC board and wherein the head covers the casing, so that the casing is protected by the head against accidentally being hit by a hammer when the probe is being hammered into the ground.

6. The measuring probe of claim 5, wherein the casing also houses:
    an antenna for wireless transmission of data and/or determining GPS data of the probe, and/or
    a battery.

7. The measuring probe of claim 1, wherein the tip and/or the head extends in longitudinal direction beyond the second member.

8. The measuring probe of claim 1, wherein the first member has, relative to the second member, a high impact strength, or the second member has, relative to the first member, a high impact strength.

9. The measuring probe of claim 1, wherein the second member embraces the first member.

10. The measuring probe of claim 1, wherein the elongate body has:
    a length which is larger than 45 centimeters, preferably larger than 55 centimeters and even more preferably larger than 65 centimeters; and/or
    a maximal thickness of 2.54 centimeters, preferably a maximal thickness of 2 centimeters, and even more preferably a maximal thickness of 1.8 centimeters.

11. The measuring probe of claim 1, wherein the head is connected to the first member-such that the axis of the first member and the axis of the head coincide.

12. The measuring probe of claim 1, wherein the head and its connection point with the first member coincide with the axis of the first member.

13. The measuring probe of claim 1, wherein the tip is connected to the first member such that the axis of the first member and the axis of the tip coincide.

14. The measuring probe of claim 1, wherein the first member comprises or is of an engineered stiff polymer material, and/or the second member comprises a fiber-reinforced material and/or carbon based material.

15. The measuring probe of claim 1, wherein the probe is provided with an IC board and comprises electrical connections extending from the respective electrodes to the IC board.

16. The measuring probe of claim 1, wherein the parameter relates to at least one of: moisture content in the soil, pH, temperature, salinity, capacity, electrical conductivity.

17. A method of bringing into the ground a measuring probe, for measuring a soil parameter at a level deeper than 15 cm in the ground, the probe having an elongate body with a tip as a leading end and a head configured to be hammered on for forcing the probe into the ground, as a trailing end, the elongate body including a plurality of electrodes with which the measuring probe is configured to measure the soil parameter after installation into the ground, the plurality of electrodes being located between the tip and the head and separated in a longitudinal direction of the elongate body, the plurality of electrodes including multiple sets of electrodes positioned at different axial positions in the longitudinal direction of the elongate body, and the elongate body having a first member and a second member which each extend in the longitudinal direction of the elongate body, the first member being connected to the head;

the method comprising:

placing the tip onto the ground;

hammering on the head and thereby forcing the probe into the ground until the probe is sufficiently deep into the ground to measure the soil parameter at a level deeper than 15 cm in the ground, with the second member providing resistance against bending of the probe when the tip advances into the ground.

18. The method of claim 17, wherein the second member provides resistance against bending of the first member when the tip is advanced into the ground by hammering on the head.

19. A method for producing a measuring probe that is configured to be advanced into ground by hammering it and that is configured to then measure a soil parameter at a level deeper than 15 cm in the ground, the method comprising:

providing a pipe-shaped member;

arranging into the pipe-shaped member a plurality of electrodes and/or electrical connections separated in a longitudinal direction of the pipe-shaped member, the plurality of electrodes including multiple sets of electrodes positioned at different axial positions in the longitudinal direction of the pipe-shaped member;

bringing into the pipe-shaped member a material having a composition, wherein the material is in a flowable condition during the bringing in; and letting the material harden after the bringing in.

* * * * *